US 6,557,426 B2

(12) United States Patent
Reinemann, Jr. et al.

(10) Patent No.: US 6,557,426 B2
(45) Date of Patent: May 6, 2003

(54) METHOD AND APPARATUS FOR TESTING SUTURE ANCHORS

(76) Inventors: Richard L. Reinemann, Jr., 30 Valley Rd., Dover, MA (US) 02030; Keith M. Orr, 42 8th St. Suite 3209, Charlestown, MA (US) 02129

( * ) Notice: Subject to any disclaimer, the term of this patent is extended or adjusted under 35 U.S.C. 154(b) by 0 days.

(21) Appl. No.: 09/775,135

(22) Filed: Feb. 1, 2001

(65) Prior Publication Data

US 2001/0032517 A1 Oct. 25, 2001

Related U.S. Application Data

(60) Provisional application No. 60/179,518, filed on Feb. 1, 2000.

(51) Int. Cl.⁷ .................................... G01L 1/26
(52) U.S. Cl. .................................... 73/862.393
(58) Field of Search ............................. 73/826, 152.17, 73/768, 783; 606/215, 60, 57, 232, 72

(56) References Cited

U.S. PATENT DOCUMENTS

| 5,585,555 | A | * | 12/1996 | McRae ..................... 73/152.17 |
| 5,665,110 | A | | 9/1997 | Chervitz et al. |
| 5,782,866 | A | | 7/1998 | Wenstrom, Jr. |
| 5,843,087 | A | | 12/1998 | Jensen et al. |
| 5,921,986 | A | * | 7/1999 | Bonutti ..................... 606/60 |
| 5,944,739 | A | | 8/1999 | Zlock et al. |
| 5,948,000 | A | | 9/1999 | Larsen et al. |
| 5,948,001 | A | | 9/1999 | Larsen |
| 5,951,559 | A | * | 9/1999 | Burkhart ..................... 606/73 |
| 5,988,171 | A | * | 11/1999 | Sohn et al. .................. 128/848 |
| 5,993,458 | A | * | 11/1999 | Vaitejunas et al. .......... 606/104 |
| 5,993,459 | A | | 11/1999 | Larsen et al. |
| 5,993,477 | A | * | 11/1999 | Vaitejunas et al. .......... 606/232 |
| 6,007,566 | A | | 12/1999 | Wenstrom, Jr. |
| 6,027,523 | A | | 2/2000 | Schmieding |
| 6,117,160 | A | * | 9/2000 | Bonutti ..................... 606/215 |
| 6,146,407 | A | * | 11/2000 | Krebs ..................... 606/232 |

FOREIGN PATENT DOCUMENTS

EP    0908143 A1    4/1999

OTHER PUBLICATIONS

Mitek Product Reference Guide, (c) 1998.
Sotereanos, Dean G., Rotator Cuff Repair Using Panalok RC Absorbable Anchor.
Mastering the Art, Mitek Surgical Products, Inc., (c) 1995.
Mitek Modified Technique slide presentation, pp. 1–41.
Sotereanos, Dean G., Rotator Cuff Repair Using Panalok RC Absorbable Anchor, (c) 1998, pp. 1–4.

* cited by examiner

Primary Examiner—Max Noori
(74) Attorney, Agent, or Firm—Cesari and McKenna, LLP

(57) ABSTRACT

A system for determining whether sutures and/or bone anchors satisfy some minimum strength threshold. The system includes a handle that contains a sensor for measuring forces or loads (e.g., a strain gauge), an indicator, and a controller. The controller is coupled to the sensor and the indicator. During use, a surgeon installs an anchor into a patient's bone. To test the strength of the anchor, the sensor is connected to the anchor preferably by some mechanical linkage, such as a rod or shaft. The surgeon then pulls on the handle. By pulling on the handle, a corresponding force is applied to the anchor through the mechanical linkage. As the surgeon pulls, the controller receives a signal from the sensor that is proportional to the force or load being applied to the anchor. The controller compares the sensor signal with some pre-determined threshold. When the signal exceeds the threshold, the controller activates the indicator, thereby alerting the surgeon that the anchor has withstood the requisite load or force, and is thus securely attached to the patient's bone.

22 Claims, 7 Drawing Sheets

METHOD AND APPARATUS FOR TESTING SUTURE ANCHORS

CROSS-REFERENCE TO RELATED APPLICATIONS

The present application claims priority from U.S. Provisional Patent Application Ser. No. 60/179,518, which was filed on Feb. 1, 2000, by Richard Reinemann, Jr. and Keith Orr for a METHOD AND APPARATUS FOR TESTING SUTURE ANCHORS, which is hereby incorporated by reference.

BACKGROUND OF THE INVENTION

1. Field of the Invention

This invention relates to systems for anchoring tissue to bone, and more specifically, to a system for testing the strength of sutures and anchors.

2. Background Information

Systems and devices for anchoring sutures to bone are commonly used in medical or surgical operations. Anchored sutures are typically used to attach soft tissue, such as is ligaments, tendons and muscles, to bone or to attach inanimate objects, such as prostheses, to bone. The attachment may be intended to hold the tissue to a bone long enough for healing to occur or for a more extended period of time (e.g., for the life of the patient). Alternatively, the attachment may be intended to hold tissue in place temporarily (e.g., only during the surgical procedure).

Conventional suture anchors are typically inserted into a bore or hole that has been previously drilled into the bone. Alternatively, they can be driven directly (e.g., hammered or screwed) into the bone in which no previous bore or hole has been made. Most bone anchors include some type of mechanism, such as ridges, threads, spikes, barbs, etc., that extend from the anchor and are intended to firmly attach the anchor to the bone. Many operations require the installation of multiple anchors in the patient's bone. Once the anchor has been secured to the bone, the suture(s) can then be attached, typically by knots, to the anchor. Alternatively, the sutures may be pre-attached to the anchor before it is installed into the bone.

Installation tools, specifically designed to install bone anchors, are also known. These tools typically assist the surgeon in inserting the anchors into the pre-formed bores or holes or in driving the anchors into the bone.

Depending on the tissue being secured, the load imposed on sutures and the corresponding anchors can vary significantly. The load on sutures and anchors can also vary depending on the patient. For example, for a given procedure, the loads imposed on sutures and anchors by a professional athlete may be significantly greater than the loads imposed by others and far less than might be imposed by the elderly. The loads imposed on the sutures and anchors may result in failures. That is, the anchors can be pulled from the bone or the sutures may break. Since anchors are relatively small and can be installed in arthroscopic surgeries, it can be difficult for surgeons to evaluate how well the installation has been done. In addition, unknown to the surgeon, the anchors can be installed in weakened bone mass precipitating a failure. Furthermore, the sutures may be "knicked" or otherwise damaged during installation compromising their strength.

SUMMARY OF THE INVENTION

Briefly, the invention is directed to a system for ensuring that sutures and anchors satisfy some minimum strength threshold in vivo (e.g., during the respective operation or procedure). The invention includes a handle that contains a sensor or transducer for measuring forces or loads (e.g., a strain gauge), an indicator, and a controller. The controller is arranged in communicating relationship with the sensor and the indicator. During use, a surgeon installs an anchor into a patient's bone. To test the strength of the anchor, the sensor is connected to the anchor preferably by some mechanical linkage, such as a rod or shaft. The surgeon then pulls on the handle. By pulling on the handle, a corresponding force is applied to the anchor through the mechanical linkage, which may extend from the handle. As the surgeon pulls, the controller receives a signal from the sensor that is proportional to the force or load being applied to the anchor. In the illustrative embodiment, the controller is configured to compare the sensor signal to some predetermined threshold. When the signal exceeds the threshold, the controller activates the indicator (which may be a visual or audio indicator), thereby alerting the surgeon that the anchor has withstood the requisite load or force, and is thus securely attached to the patient's bone.

The surgeon may also, or in the alternative, test the strength of the sutures and the anchor together. In this case, the surgeon connects one or more sutures to the anchor, unless the sutures were pre-attached to the anchor. The sutures are then connected to the sensor either directly or through some linkage. Again, the surgeon pulls on the housing of the system, thereby applying a corresponding force to the sutures. When the force or load applied to the sutures exceeds the pre-determined threshold, the controller activates the indicator.

In another embodiment of the invention, the handle may further contain an input device that is also in communicating relationship with the controller. By manipulating the input device, the surgeon can adjust the threshold utilized by the controller. In this embodiment, the controller activates the indicator when the sensor signal exceeds the threshold as set by the input device. In this way, the surgeon can select the particular force or load that the anchor or sutures must satisfy during the operation or procedure.

In yet another embodiment, the system includes a drive mechanism that allows the surgeon to test the strength of the anchor or sutures without having to pull on the handle. The drive mechanism includes a support that extends from the handle and engages the patient. The drive mechanism further includes an actuator that moves the sensor away from the patient. In use, the anchor or sutures are connected to the sensor. The actuator is then started, pulling the sensor away from the patient, thereby imposing a force or load onto the anchor or sutures. When the signal from the sensor exceeds the threshold, indicating that the force or load on the anchor or sutures exceeds the minimum level, the controller activates the indicator.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
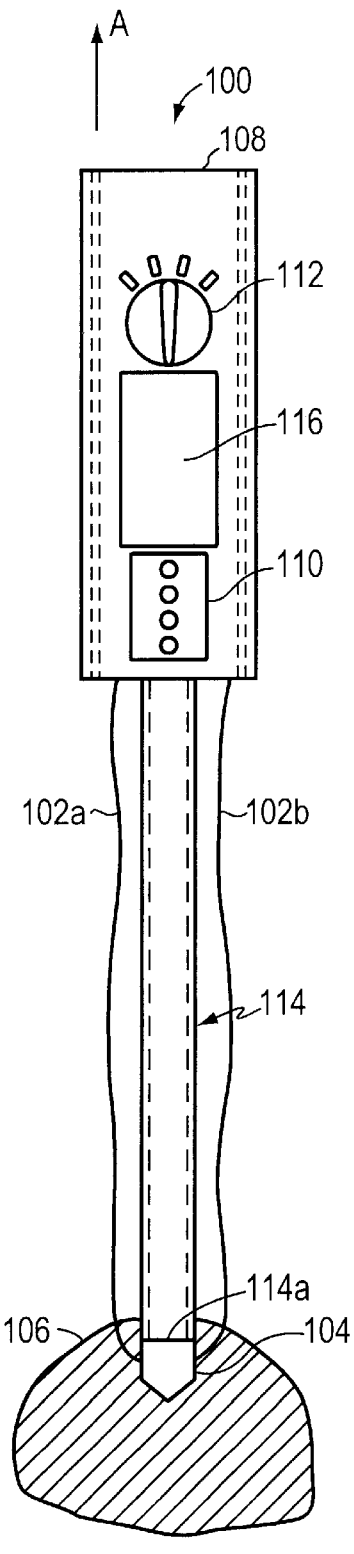
FIG. 1 is an elevation view of the system of the present invention.

FIG. 1 is an elevation view of a system 100 for testing the strength of sutures 102a, 102b and/or an anchor 104 to which the sutures 102a, 102b are attached. The anchor 104 is preferably installed into a patient's bone structure 106 in a conventional manner. The system 100 includes a handle 108. Mounted to the handle 108 is an indicator 110 and an input device, such as a dial 112. Extending from the handle 108 may be a mechanical linkage, such as a shaft 114 having a distal end 114a relative to the handle 108. Handle 108 may also include a removable panel 116 for providing access to the interior of the handle 108. As described below, the distal end 114a of the shaft 114 can be removably connected to the anchor 104.

Figure 2:
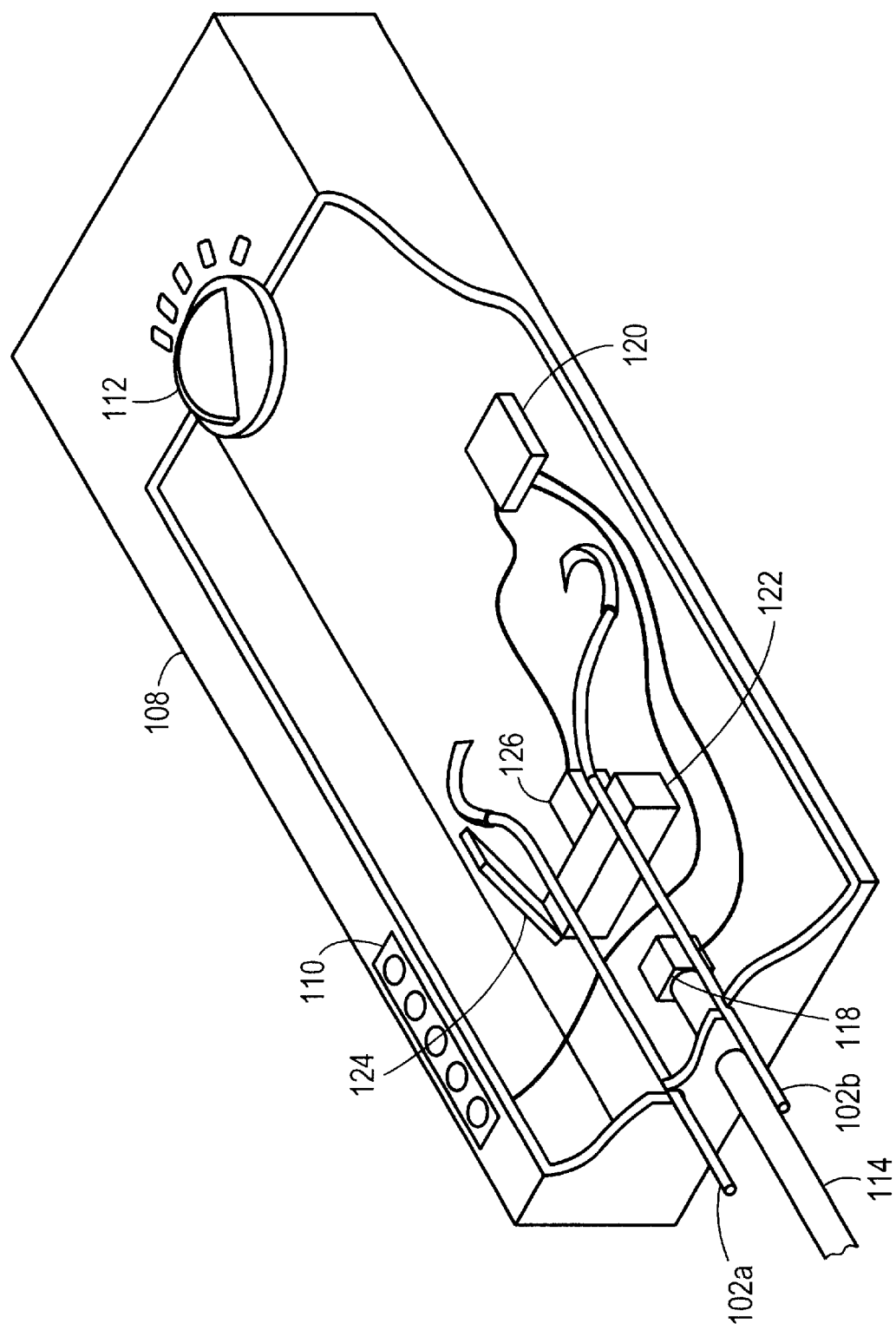
FIG. 2 is a partial, break-away view of the system of FIG. 1.

FIG. 2 is a break-away view of the handle 108. Disposed within the handle 108 are a first sensor 118 and a controller 120. Also disposed within the handle 108 is a pinch bar 122 having a latch 124 for securing the sutures 102a, 102b, which may be received inside the handle 108 through corresponding slots or holes. Attached to the pinch bar 122 preferably opposite to where the sutures 102a, 102b are received is a second sensor 126 that is similarly mounted to the interior of the handle 108 like first sensor 118. The controller 120, which is preferably a microprocessor, is connected to the first sensor 118, the second sensor 126, the indicator 110 and the dial 112 by corresponding wires. The first and second sensors 118, 126 are preferably each configured to generate corresponding signals for receipt by the controller 120 that are responsive to the force or load at the respective sensor 118, 126. The sensors 118, 126, for example, may be strain gauges mounted to corresponding blocks of material, such as steel.

The first sensor 118 is connected to shaft 114, which may also be received within the handle 108 through a corresponding slot or hole. First sensor 118 is configured and arranged to generate a signal that is proportional or responsive to the force or load on the shaft 114. Pinch bar 122 is preferably only connected to the interior of the handle 108 through the second sensor 126. The second sensor 126, moreover, is configured and arranged so that its signal is proportional or responsive to the load or force on the pinch bar 122, which, in turn, corresponds to the force or load on the sutures 102a, 102b. Those skilled in the art will recognize that other types of sensors besides strain gauges and that other configurations and arrangements may also be utilized.

A suitable power source, such as a battery (not shown), is preferably used to power the controller 120, the sensors 118, 126 and the indicator 110. Alternatively or additionally, the system could be configured to receive external power.

It should be understood that the one or more of the components shown inside of the handle 108, such as the pinch bar 122, could be disposed on the outside of the handle 108 as well.

The system 100 is preferably used as follows. The surgeon first installs the anchor 104 (FIG. 1) into the patient's bone structure 106 in a conventional manner and attaches the sutures 102a, 102b to the anchor 104. It should be understood that some sutures are pre-attached to the anchor. To test the strength of the anchor 104, the surgeon removably attaches the distal end 114a of the shaft 114 to the anchor 104.

Figure 3:
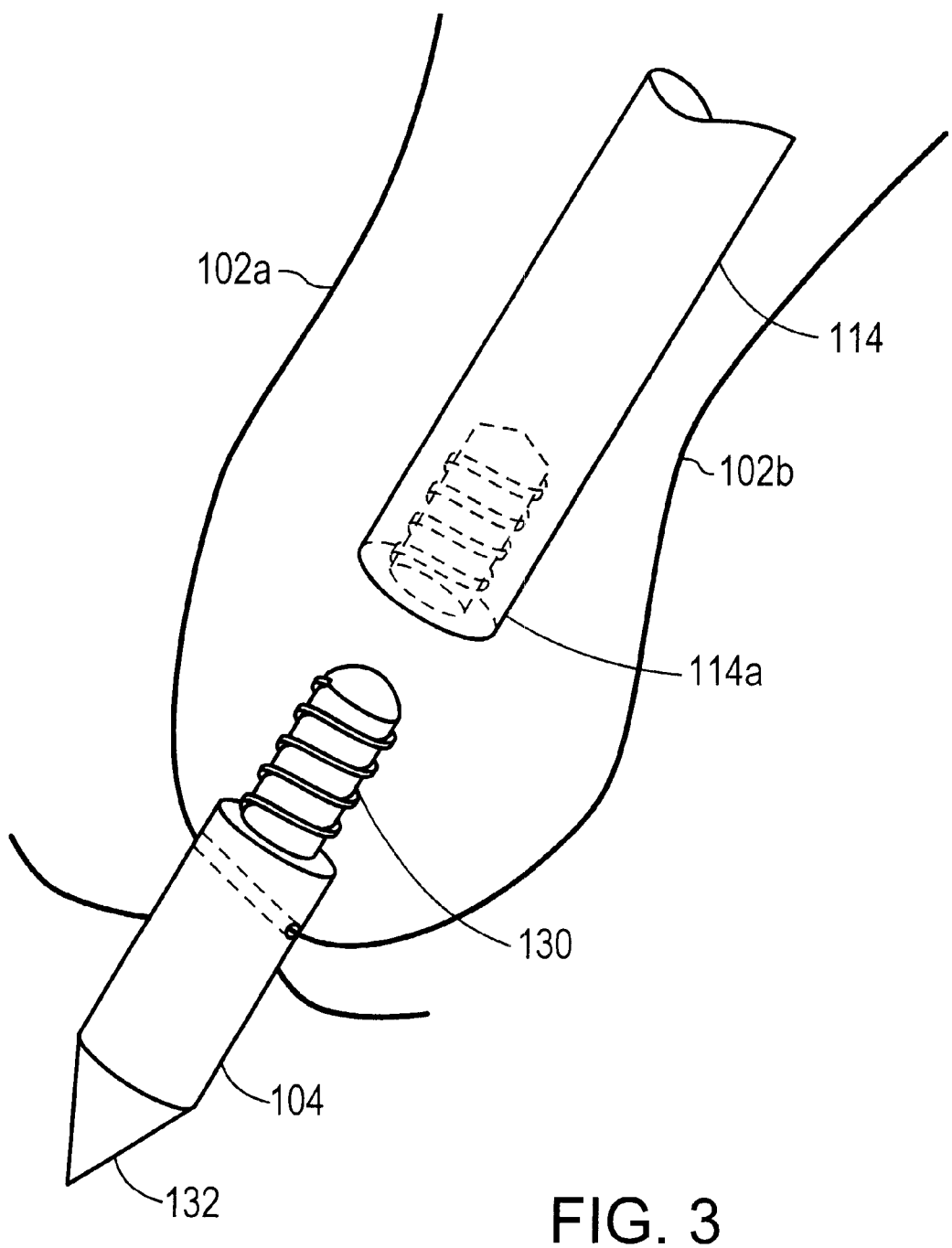
FIG. 3 is a partial, perspective view of the system of FIG. 1.

FIG. 3 is a partial, perspective view of the system 100 showing a preferred attachment mechanism. Specifically, anchor 104 includes a threaded stud 130 that extends opposite a tip 132 of the anchor 104. This tip 132 is designed to be received into the bore or hole formed in the patient's bone structure 106 (FIG. 1). A hole 134 tapped with threads extends into the shaft 114 at distal end 114a. The threads of hole 134 are arranged to matingly engage the stud 130 of anchor 104. Thus, by rotating shaft 114 relative to the anchor 104, the shaft 114 can be removably secured to the anchor 104. Those skilled in the art will understand that other attachment means may be employed (e.g., hook and loop, etc.).

After attaching shaft 114 to anchor 104, the surgeon preferably adjusts the dial 112 to select some minimum force that the anchor 104 should withstand. That is, the dial 112 may be moved between a minimum force value and a maximum force value. The setting of the dial 112 is monitored by the controller 120.

The surgeon then pulls the handle 108 away from the anchor 104 preferably as shown by arrow A (FIG. 1). By pulling on the handle 108, a force is applied to the anchor 104 by means of the shaft 114, which is connected to the first sensor 118, which, in turn, is connected to the handle 108. The signal generated by the first sensor 118, which is received at the controller 120, is proportional to the force being applied to the anchor 104. The controller 120 compares this signal to a threshold that it determines as a function of the setting of the dial 112. In other words, the controller 120 has a threshold that is set in response to the position of the dial 112. When the signal from the first sensor 118 exceeds the threshold as determined by the position of the dial 112, the controller activates the indicator 110. The indicator may be a visual indicator (e.g., a light, a bank of lights, etc.) and/or an aural indicator (e.g., a device that emits a "beep" sound, etc.). When the surgeon sees that the indicator 110 has been activated, he or she knows that the anchor 104 has withstood the desired force. The surgeon may then continue with the operation or procedure using the anchor 104.

If, during the testing of the anchor 104, it slips or pulls out of the bone structure 106, as detected by the surgeon through movement of the handle 108 relative to the bone structure 106 before activation of the indicator 110 by the controller 120, then the surgeon knows that the anchor 104 was unable to withstand the desired load or force. In this case, the surgeon may take any number of responsive actions, such as re-installing the anchor, using a new anchor that has better securing elements, selecting a new location for the anchor, etc.

The controller 120 and dial 112 are preferably designed to provide a useful range of force thresholds (typically from 1 to 50 pounds force). It should be understood that the controller 120 may be configured with a pre-set threshold. In this embodiment, there is no input device, such as dial 112, to modify the threshold of the controller 120.

To test the strength of the sutures 102a, 102b and anchor 104 in combination, the process is as follows. Instead of attaching the distal end 114a of the shaft 114 to the anchor 104, the surgeon opens the removable panel 116 and lifts the latch 124 of the pinch bar 122. The surgeon then feeds the sutures 102a, 102b between the latch 124 and pinch bar 122 and closes the latch 124, thereby securing the sutures 102a, 102b to the pinch bar 122. Next, the surgeon adjusts the dial 112 to the desired force or load that the sutures 102a, 102b and anchor 104 are to meet. The surgeon then pulls on the handle 108 in the direction of arrow A. As the handle 108 is pulled away from the anchor 104, the sutures 102a, 102b, will become taught. As the handle 108 continues to be pulled in the direction of arrow A an increasing force or load will be applied to the sutures 102a, 102b by means of the pinch bar 122, which is connected to the second sensor 126, which, in turn, is connected to the handle 108.

The signal generated by the second sensor 126, which is also received at the controller 120, is proportional to the force being applied to the sutures 102a, 102b. The controller 120 compares this signal to the threshold specified by the position of the dial 112. When the signal from the second sensor 126 exceeds this threshold, the controller 120 activates the indicator 110. Activation of the indicator 110, informs the surgeon that the sutures 102a, 102b and anchor 104 have withstood the desired force. The surgeon may then continue with the operation or procedure using the anchor 104 and sutures 102a, 102b. If the sutures 102a, 102b break, or anchor 104 slips or is pulled out of the bone structure 106 before the indicator 110 is activated, then the surgeon knows that the sutures 102a, 102b or anchor 104, as the case may be, was unable to withstand the desired load or force.

In the preferred embodiment, the system 100 may be pre-assembled with the sutures 102a, 102b already attached to the pinch bar 122. Thus, the surgeon can easily test the sutures 102a, 102b by simply not attaching the shaft 114 to the anchor 104.

In an alternative embodiment, the system may include a mechanical, spring-based pull gauge in place of the sensor and controller. The pull gauge preferably includes a scale which has been calibrated to display the force being applied to the spring based on its deflection (i.e., elongation). Here, the surgeon would attach one end of the pull gauge to the anchor or the sutures and pull until the desired force, as shown on the scale, is imposed on the anchor or sutures without adverse result.

Figure 4:
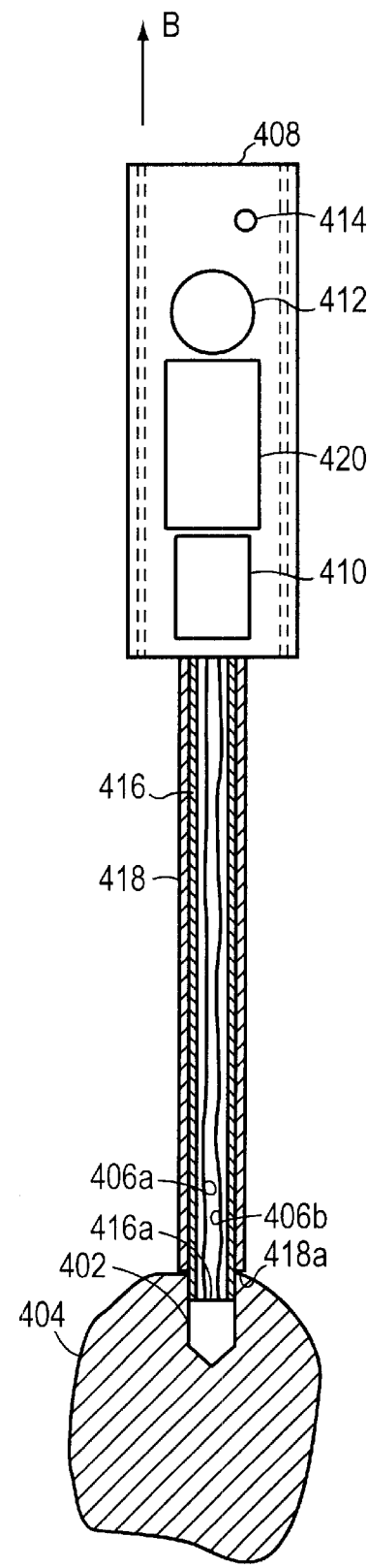
FIG. 4 is an elevation view of another embodiment of the present invention.

FIG. 4 is an elevation view of a system 400 in accordance with another embodiment of the present invention. System 400 is preferably used to test the strength of an anchor 402 installed in a patient's bone structure 404 and/or sutures 406a, 403b attached to the anchor 402 without having to be manually pulled by a surgeon. The system 400 includes a handle 408. Mounted to the handle 408 is an indicator 410, an input device, is such as a dial 412, and a start button 414. Extending from the handle 408 may be a mechanical linkage, such as a shaft 416 having a distal end 416a relative to the handle 408. The distal end 416a of the shaft 416 is preferably connected to the anchor 402. Shaft 416 may include a longitudinal slot (not shown) so that the sutures 406a, 406b may be fed through the inside of shaft 416. The system 400 further includes a support member, such as rod 418, that also extends from the handle 408. The rod 418 has a distal end 418a relative to handle 408 that engages or is in close proximity to a surface of the bone structure 404 into which the anchor 402 has been installed. The rod 418 may surround and partially or completely enclose the shaft 416. Handle 108 may also include a removable panel 420 for providing access to its interior.

Figure 5:
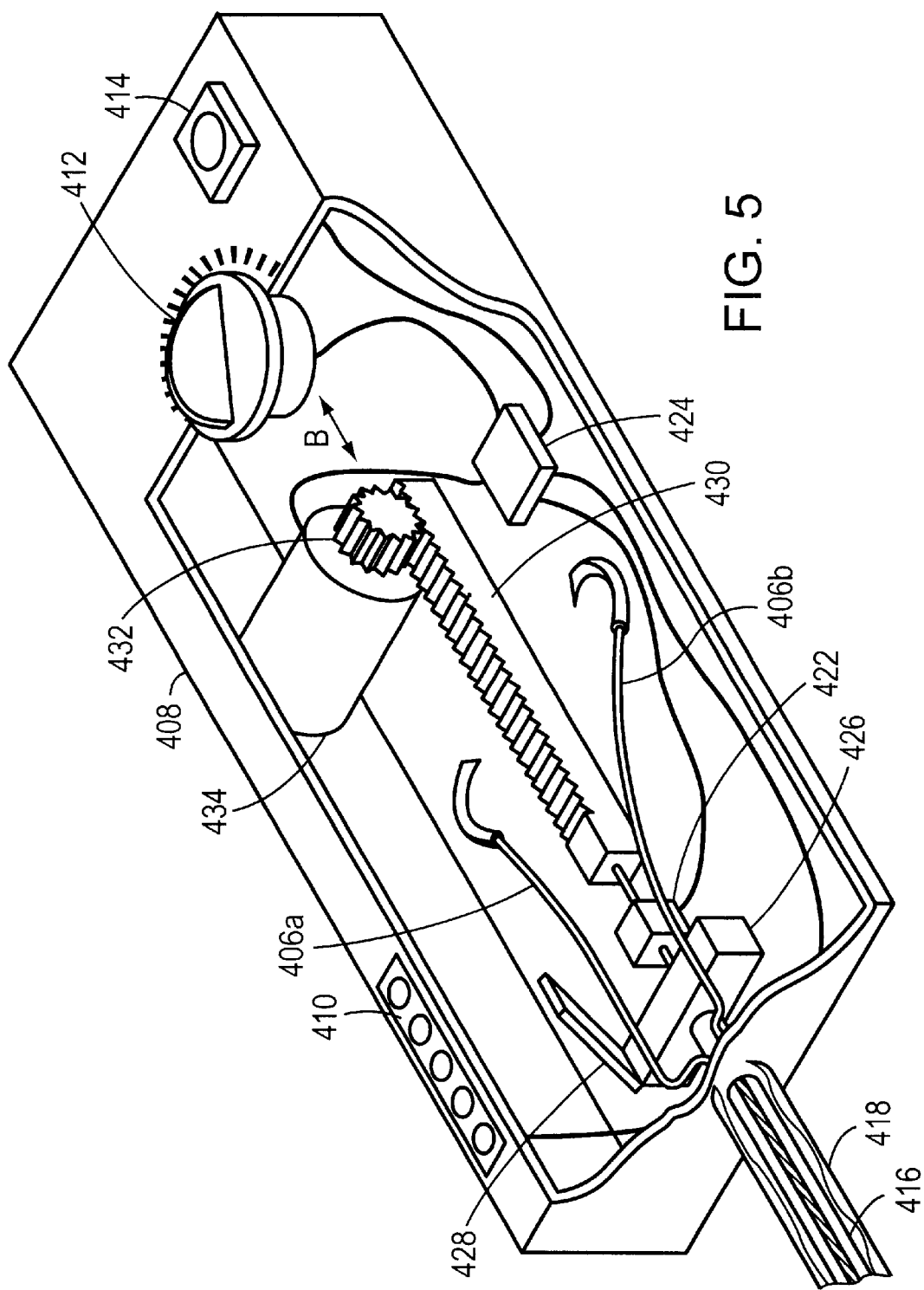
FIG. 5 is a partial, break-away view of the system of FIG. 4.

FIG. 5 is a break-away view of the handle 408 of FIG. 4. Disposed within the handle 408 are a sensor 422, a controller 424, and a pinch bar 426 having a latch 428 for securing the sutures 406a, 406b, which may be received inside the handle 408. Shaft 416 is received inside the handle 408 and is preferably attached to the pinch bar 426. Also attached to the pinch bar 426, opposite shaft 416, is the sensor 422. Attached to the sensor 422, opposite the pinch bar 426, is a rack 430 having a plurality of teeth. The rack 430 preferably engages a drive gear 432 powered by a motor 434. Motor 434 is preferably mounted to the inside of, and is fixed relative to, the handle 408. As described in more detail below, operation of the motor 434 and thus drive gear 432 causes rack 430 to move linearly as shown by arrow B. Movement of the rack 430, in turn, causes corresponding movement of the sensor 422, pinch bar 426 and shaft 416. The controller 424, which is preferably a microprocessor, is connected to the sensor 422, the indicator 410, the dial 412, the motor 434 and the start button 414 by corresponding wires. The sensor 422 is preferably configured to generate corresponding signals for receipt by the controller 424 that are responsive to the force or load at the sensor 432. Sensor 432, for example, may be a strain gauge mounted to a corresponding block of material, such as steel.

The system 400 is preferably used as follows. The surgeon first installs the anchor 402 (FIG. 4) into the patient's bone structure 404 in a conventional manner, attaches the sutures 406a, 406b to the anchor 402 and feeds them up through the slot in the shaft 416. It should be understood that some sutures are pre-attached to the anchor. To test the strength of the anchor 402, the surgeon removably attaches the distal end 416a of the shaft 416 to the anchor 402. The surgeon then adjusts the dial 412 to a selected minimum force or load that the anchor 402 should withstand. That is, the dial 412 may be moved between a first position corresponding to some minimum force value and a second position corresponding to some maximum force value. The setting of the dial 412 is monitored by the controller 424.

Next, the surgeon places the distal end 418a of the rod in close proximity to or in direct contact with the surface of the bone structure 404 into which the anchor 402 has been placed. Rod 418 may be formed from multiple pieces that cooperate with each other in a telescopic fashion. For example, the rod 418 may include two pieces that threadably or slidably engage each other. By rotating or sliding one piece relative to the other, the surgeon can elongate or shorten the rod 418 to the desired length. After adjusting the rod 418 to the desired length, e.g., so that it contacts or nearly contacts the bone structure 404, the surgeon then presses the start button 414.

Controller 424 detects the activation of start button 414 and, in response, controller 424 activates motor 434, which turns drive gear 432. Rotation of the drive gear 432 causes the rack 430 to move linearly in the direction of arrow B. Controller 424 preferably directs the motor 434 to turn the drive gear 432 in a counter-clockwise direction as shown by FIG. 4 so that movement of the rack 430 draws the shaft 416 further inside the handle 408. As the shaft 416 is drawn further inside the handle 408, the distal end 418a of the rod 418 will contact the surface of the bone structure 404 preventing the shaft 416 from moving any further. Due to the torque of motor 434, however, the drive gear 432 will continue to pull on the rack 430. By continuing to pull on the rack 430, the motor 434 imposes an increasing force or load through the sensor 422, pinch bar 426, and shaft 416 to the anchor 402. The level of this increasing force is continuously detected by the sensor 422, which provides its signal to the controller 424.

The controller 424 compares the signal from the sensor 422 to a threshold that it determines based on the setting of the dial 412. When the signal from the sensor 422 exceeds the threshold, the controller 424 activates the indicator 410.

The indicator 410 may be a visual indicator (e.g., a light, a bank of lights, etc.) or an aural indicator (e.g., a device that emits a "beep" sound, etc.). When the surgeon sees that the indicator 410 has been activated, he or she knows that the anchor 402 has withstood the desired force. In response to reaching the threshold, the controller 424 may be further configured to deactivate the motor 434. Alternatively or in addition, surgeon may press button 414 again, causing the controller 424 to de-activate the motor 434. The surgeon may then continue with the operation or procedure using the anchor 402.

To test the strength of the sutures 406a, 406b and anchor 402 in combination, the process is as follows. Instead of attaching the distal end 416a of the shaft 416 to the anchor 402, the surgeon opens the removable panel 420 and lifts the latch 428 of the pinch bar 426. The surgeon then feeds the sutures 406a, 406b between the latch 428 and pinch bar 426 and closes the latch 428, thereby securing the sutures 406a, 406b to the pinch bar 426. Next, the surgeon adjusts the dial 412 to the desired force or load that the sutures 406a, 406b and anchor 402 are to meet. The surgeon then places the distal end 418a of the rod 418 in close proximity to or in direct contact with the surface of the bone structure 404 into which the anchor 402 has been placed, and presses the start button 414 on handle 408.

Controller 424 activates motor 434, causing drive gear 432 to turn and rack 430 to move linearly in the direction of arrow B. Again, controller 424 preferably directs the motor 434 to turn the drive gear 432 in a counter-clockwise direction so that movement of the rack 430 draws the sutures 406a, 406b clamped to the pinch bar 426 further inside the handle 408. As the sutures 406a, 406b are drawn further and further inside the handle 408, the distal end 418a of the rod 418 will contact the surface of the bone structure 404. As the sutures 406a, 406b continue to be pulled inside the handle 408, they will eventually become taught, preventing the rack 430 from moving any further. Due to the torque of motor 434, however, the drive gear 432 will continue to pull on the rack 430. By continuing to pull on the rack 430, the motor 434 imposes an increasing force or load through the sensor 422, and pinch bar 426 to the sutures 406a, 406b. The level of this increasing force is continuously detected by the sensor 422, which provides its signal to the controller 424.

The controller 424 compares the signal from the sensor 422 to a threshold that it determines based on the setting of the dial 412. When the signal from the sensor 422 exceeds the threshold, the controller 424 activates the indicator 410. The indicator 410 may be a visual indicator. When the surgeon sees that the indicator 410 has been activated, he or she knows that the sutures 406a, 406b and anchor 402 have withstood the desired force or load. In response to reaching the threshold, the controller 424 may de-activate the motor 434, or the surgeon may press button 414 again, causing the controller 424 to deactivate the motor 434. The surgeon may then continue with the operation or procedure using the sutures 406a, 406b and anchor 402.

If the sutures 406a, 406b break or the anchor 402 slips or pulls out of the bone structure 404 before the indicator 410 is activated, then the surgeon knows that the sutures 406a, 406b and/or anchor 402 were unable to withstand the desired load or force. In this case, the surgeon may take any number of responsive actions, such as re-installing the anchor, installing a new anchor that has better securing elements, selecting a new location for the anchor, installing new sutures, etc.

It should be understood that the system of the present invention may designed as a stand-alone unit for use in testing the strength of installed anchors and sutures or it may be built-on to conventional tools used to install anchors and/or sutures. Tools for installing or deploying bone anchors are well-known. U.S. Pat. No. 5,843,087 to Jensen et al., titled SUTURE ANCHOR INSTALLATION TOOL, issued Dec. 1, 1998, which is hereby incorporated by reference in its entirety, for example, describes a Suture Anchor Installation Tool. The present invention may be added to and/or built into the tool of U.S. Pat. No. 5,843,087.

Those skilled in the art will recognize that various alternatives may be selected or incorporated to achieve the objects of the present invention.

Figures 6, 7:
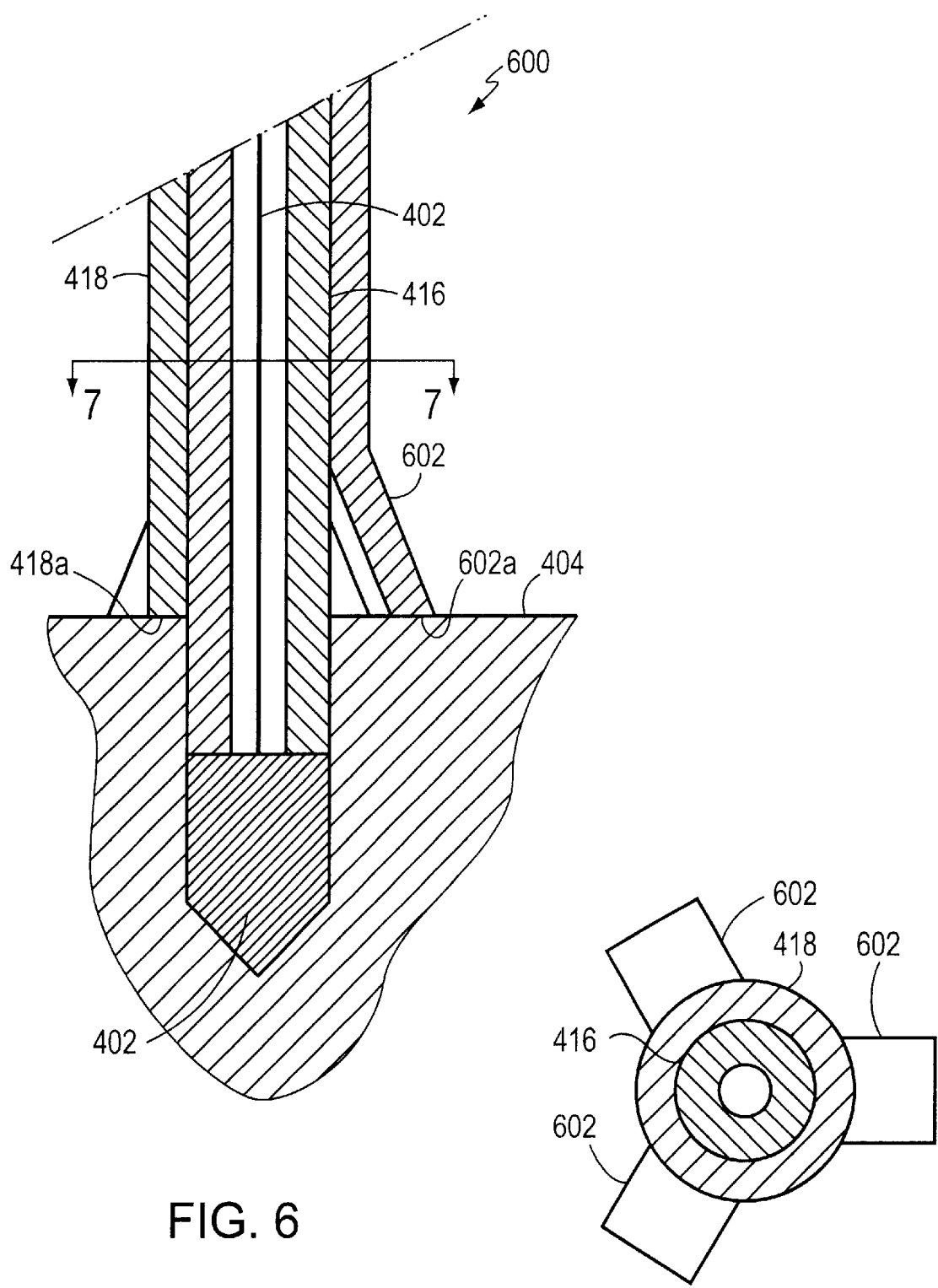
FIG. 6 is a side elevation view of another embodiment of the system of the present invention.
FIG. 7 is a cross-sectional view of the system of FIG. 6.

FIG. 6 is a side elevation view of an automatic suture/anchor tester system 600 and FIG. 7 is a cross-sectional view of the system 600 of FIG. 6 along lines 7—7. System 600 includes an inner shaft 416 coupled to an anchor 402, a suture 406 and an outer rod 418 having a distal end 418a that, in operation, is placed proximate to or in contact with the patient's bone structure 404. Attached to outer rod 418 at or near its distal end 418a are one or more braces or feet 602 which extend outwardly away from the rod 418. The feet 602 have surfaces 602a for engaging the bone structure 404 and thus improve the outer rod's stability and gripping ability when the testing of the anchor 402 and/or suture 406 is being performed.

Those skilled in the art will recognize that feet 602 may be replaced with rigid or flexible expander bars and/or with barbs that detachably engage the patient's bone structure 404. The feet 602, expander bars and/or barbs can also be configured for deployment from inside rod 418 or from its outer surface by the surgeon in case their size restricts them from being inserted into a trocar or for other reasons.

In addition to alternative arrangements to stabilize and secure the outer rod 418 to the patient's bone structure during anchor and/or suture testing, modifications or alterations may also be made to the indicator element of the invention.

For example, the indicator 110 may consist of one or more red light emitting diodes (LEDs) and one or more green LEDs. In this case, when the surgeon tests the anchor 104 and/or sutures 102, the controller 120 would activate the red LED and keep it activated until the pre-set tension is reached. At that point, the controller 120 would deactivate the red LED and activate the green LED, thereby notifying the surgeon that the anchor and/or suture passed the test. Alternatively, the controller 120 could be configured to activate the red LED if the pulling action on the handle 108 ceases before the preset tension is reached.

In another embodiment, the indicator 110 may be configured as a linear array of LEDs. As the tension on the anchor and/or sutures is increased, the controller 120 could be configured to activate more LEDs thereby providing some measure of feedback to the surgeon. In addition, a calibrated scale could be provided adjacent to the array of LEDs, thereby providing the surgeon with an indication of the actual forces being applied to the anchor and/or sutures. The scale could have a threshold indicating the point at which the anchor and/or sutures have passed the strength test.

Figure 8:
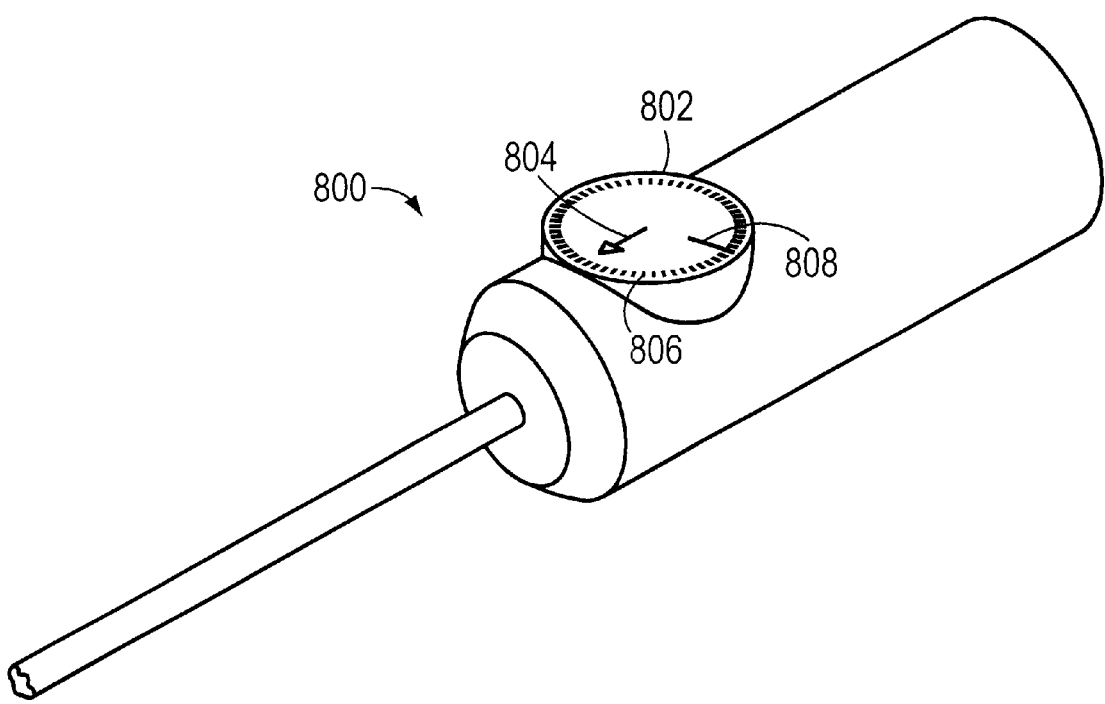
FIGS. 8 and 9 are perspective view of still further embodiments of the system of the present invention.

FIG. 8 is a perspective view of a system 800 having an analog-type gauge 802 as an indicator. Gauge 802 preferably includes a rotatable needle 804 that is controller by the controller 120 (FIG. 2) in response to the force detected by the sensor. That is, as the force measured by the sensor increases, the controller 120 rotates the needle 804 in a clockwise direction. A series of calibration marks 806 may be provided around the periphery of the gauge 802 to provide feedback to the surgeon of the forces being applied to the anchor and/or sutures. One or more threshold marks 808 that are distinguishable from the other calibration marks 806 may also be included to notify the surgeon when the anchor and/or sutures have passed the strength test.

Instead of or in addition to the analog-type gauge, the indicator could include a liquid crystal display (LCD) configured to provide a digital read-out. The controller 120, moreover, could be configured to direct the LCD to display the actual forces being applied to the anchor and/or sutures.

Those skilled in the art will also recognize that various alternatives exist for inputting a desired strength threshold to the system.

Figure 9:
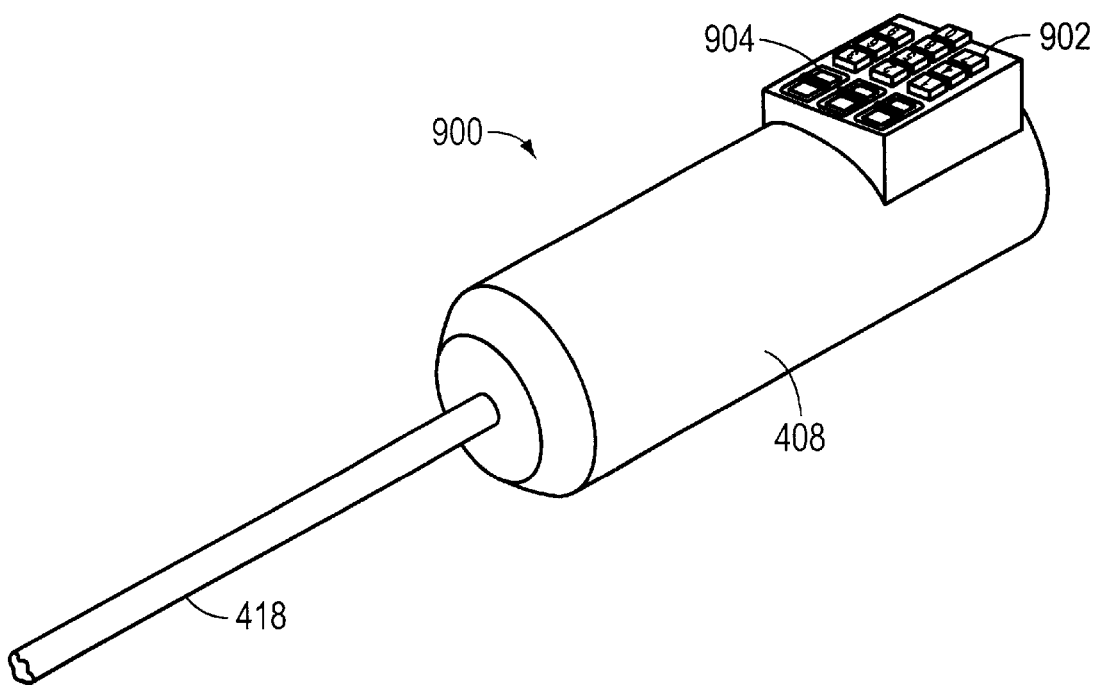

FIG. 9, for example, is a perspective view of a anchor and/or suture tester system 900 having a numeric keypad 902 as an input device. Associated with the keypad 902 may be an LCD display 904 which is under the control of the controller 120 (FIG. 2). By selecting various keys of the keypad 902, the surgeon can enter a desired force that the anchor and/or suture is to meet. The controller 120 is preferably coupled to the keypad 902 and thus receives the inputs made thereon. An enter key (not shown) could also be provided for use by the surgeon when the desired value has been entered. The values being entered at the keypad 902 can be displayed on the LCD display 904 to facilitate the operation of the system 900.

In a further alternative, the numeric keys could be replaced with up/down keys. In this case, the surgeon repeatedly presses the up/down keys until the desired force is shown in the LCD display. The enter key could then be pressed to signal to the controller 120 that the desired value has been entered.

Those skilled in the art will further recognize that all or part of the system of the present invention could be made disposable. For example, the anchor, shaft, sutures, and possibly an end cap disposed at the distal end of the shaft could be part of a disposable assembly. The handle including the electronic sensing and indicating apparatus would be non-disposable.

The foregoing description has been directed to specific embodiments of this invention. It will be apparent, however, that other variations and modifications may be made to the described embodiments, with the attainment of some or all of their advantages. For example, the system could be configured to test the strength of anchors relative to a bending moment and/or to a twisting action, among other possible loads to the anchor. Therefore, it is the object of the appended claims to cover all such variations and modifications as come within the true spirit and scope of the invention.

What is claimed is:

1. A system for resting the strength of an anchor installed into a bone, the system comprising:
    at least one sensor configured to generate a signal responsive to a force at the sensor;
    a mechanical link associated with the at least one sensor and detachably connected to the anchor that is installed into the bone for applying a force thereto in a direction away from the bone and for transmitting the applied force to the at least one sensor;
    a controller for receiving the signal generated by the at least one sensor; and
    an indicator operatively coupled to the controller, wherein the controller compares the signal received from the at least one sensor with a thresh- old, and activates the indicator when the sensor signal exceeds the threshold.

2. The system of claim 1 wherein the at least one sensor is a strain gauge.

3. The system of claim 2 wherein the indicator is a visual indicator.

4. The system of claim 3 wherein the mechanical link imposes an increasing force on the anchor, the force being detected by the at least one sensor.

5. A system for testing the strength of sutures connected to an anchor installed into a bone, the system comprising:
    at least one sensor configured to generate a signal responsive to a linear force at the sensor;
    means for connecting the sutures, that are connected to the anchor installed in the bone, to the at least one sensor;
    a controller for receiving the signal generated by the at least one sensor; and
    an indicator operatively coupled to the controller, wherein the controller compares the signal received from the at least one sensor with a threshold, and activates the Indicator when the sensor signal exceeds the threshold.

6. The system of claim 1 further comprising an input device in communicating relationship with the controller, the input device adjustable by a user to set the threshold.

7. The system of claim 6 wherein the input device is a dial that can be rotated to set the threshold.

8. The system of claim 1 further comprising a handle in which the controller is disposed, the handle configured for handheld grasping by a user.

9. The system of claim 8 wherein the handle has an outer surface and the indicator is mounted to the outer surface of the handle.

10. The system of claim 8 wherein the mechanical link has an end that is rigidly attached to the handle.

11. The system of claim 1 further comprising a drive mechanism coupled to the mechanical link, the drive mechanism configured to draw the mechanical link away from the bone.

12. The system of claim 11 further comprising a support member configured to engage the bone and to impose a counter-force on the bone in a direction opposite to the force applied by the mechanical link.

13. The system of claim 12 further comprising a handle in which the controller and the drive motor are disposed.

14. The system of claim 12 wherein the controller is operably coupled to the drive motor.

15. The system of claim 5 wherein the connecting means includes a pinch bar having a latch moveable between an open position and a closed position.

16. The system of claim 5 further comprising an input device in communicating relationship with the controller, the input device adjustable by a user to set the threshold.

17. A system for testing the strength of an anchor installed into a bone, the system comprising:
    at least one sensor configured to generate a signal responsive to a force at the sensor;
    a mechanical link associated with the at least one sensor and detachably connected to the anchor that is installed into the bone for applying a force thereto in a direction away from the bone and for transmitting the applied force to the at least one sensor;
    a controller for receiving the signal generated by the at least one sensor; and
    an indicator operatively coupled to the controller, wherein the controller activates the indicator in response to the signal received from the sensor.

18. The system of claim 17 wherein the indicator includes one or more of an aural indicator and a visual indicator.

19. The system of claim 17 further comprising a drive mechanism coupled to the mechanical link, the drive mechanism configured to draw the mechanical link away from the bone.

20. The system of claim 19 further comprising a support member configured to engage the bane and to impose a counter-force on the bone in a direction opposite to the force applied by the mechanical link.

21. An apparatus for testing the strength of an anchor installed into a bone, the apparatus comprising:

at least one sensor configured to generate a signal in response to a force;

a link associated with the at least one sensor for applying a force to the anchor which is at least in part in a direction away from the bone and for transmitting the applied force to the at least one sensor; and an indicator operably coupled to the at least one sensor, the indicator configured to activate based on the signal from the at least one sensor.

22. The apparatus of claim 21 wherein the indicator is one or more of an aural indicator and a visual indicator.

* * * * *